United States Patent [19]

Rowland

[11] 4,419,097

[45] Dec. 6, 1983

[54] ATTACHMENT FOR CATHETER TUBE

[75] Inventor: Floyd C. Rowland, Tulsa, Okla.

[73] Assignee: Rexar Industries, Inc., Tulsa, Okla.

[21] Appl. No.: 288,993

[22] Filed: Jul. 31, 1981

[51] Int. Cl.³ ............................................ A61M 25/02
[52] U.S. Cl. .................................... 604/174; 604/180;
604/352
[58] Field of Search ........... 128/294, 295, 348, 349 R, 128/132 R; 604/176–180, 349–353

[56] References Cited

U.S. PATENT DOCUMENTS

| 1,661,494 | 3/1928 | Nielsen | 128/349 R |
|---|---|---|---|
| 2,046,094 | 6/1936 | Schmidt | 128/349 R |
| 2,159,947 | 5/1939 | Gansel | 128/349 R |
| 2,213,210 | 9/1940 | Egbert | 128/349 R |
| 2,525,238 | 10/1950 | Penksa | 128/132 R |
| 2,547,758 | 4/1951 | Keeling | 128/349 B |
| 2,789,560 | 4/1957 | Weimer | 604/349 |
| 2,940,450 | 6/1960 | Witt et al. | 128/295 |
| 3,648,700 | 3/1972 | Warner | 128/294 |
| 3,730,187 | 5/1973 | Reynolds | 128/349 R |
| 3,742,953 | 7/1973 | Lee | 128/295 |
| 4,337,775 | 7/1982 | Cook et al. | 128/295 X |

FOREIGN PATENT DOCUMENTS 649451 8/1937 Fed. Rep. of Germany ... 128/349 R

Primary Examiner—Dalton L. Truluck
Attorney, Agent, or Firm—Head, Johnson & Stevenson

[57] ABSTRACT

An attachment for catheter device for reducing discomfort for a male patient and comprising an open ended substantially cylindrical housing for receiving a male member therein, and having a closed end apertured for receiving a catheter tube therethrough, the open end of the housing being provided with axially extending fingers for facilitating securing of the housing thereon, the housing functioning for reducing relative movement between the catheter tube and the male member for relieving discomfort of the patient.

10 Claims, 8 Drawing Figures

ATTACHMENT FOR CATHETER TUBE

BACKGROUND OF THE INVENTION

1. Field of the Invention

This invention relates to improvements in catheter tubes and more particularly, but not by way of limitation, to an attachment for a catheter tube for reducing discomfort of a male patient.

2. Description of the Prior Art

Many bed ridden patients, or the like, are fitted with catheter devices for facilitating the discharge of urine. The catheter devices normally include an elongated tube member in open communication with a collecting vessel. The tube is usually inserted through the urethra of the patient and is provided with an open end for receiving the urine therein whereby the urine may be directed into the vessel. Any suitable means is provided for retaining the tubing in position within the body of the patient. Male patients who are required to use catheters frequently have many problems. For example, any movement of the patient usually causes relative movement of the flesh surrounding the catheter tube, and may result in painful tearing of the flesh, or otherwise creating irritations. The disadvantages will be readily apparent.

SUMMARY OF THE INVENTION

The present invention contemplates a novel attachment for catheter tubes which is particularly designed and constructed for alleviating the foregoing disadvantages. The novel attachment comprises an open type housing having one end open for receiving the male member therein, and the opposite end closed by an arcuate or partially spherical end wall having a centrally disposed aperture provided therein. The aperture may be provided with an axially extending open ended tube member extending axially outwardly therefrom, if desired, for receiving the catheter tube therethrough, and the open end of the housing is preferably provided with a plurality of fingers extending axially outwardly therefrom for facilitating securing of the housing in position on the male member. A suitable elongated strap member having suitable engagement means provided thereon may be wrapped around the outer periphery of the fingers for securing the housing in position. The engagement mean may be Velcro (a trademark of Velcro Corporation) in order to provide ease and speed of installation and removal of the strap.

During use of the device, the catheter tube may be inserted through the apertured end of the housing member prior to insertion of the tube into the urethra, thus, positioning the housing between the collecting vessel and the outer end of the tube. The outer end of the tube may then be inserted into the urethra in the usual manner, and when the tube has been properly positioned for the patient, the housing may be moved longitudinally along the tube for placing of the housing on the outer end of the male member. The housing may then be secured in position by wrapping the locking strap around the outer periphery of the fingers. The housing then functions for substantially precluding relative movement between the tube and the male member, thus alleviating the discomfort usually incurred, particularly during prolong usage of a catheter. The novel attachment is simple and efficient in operation and economical and durable in construction.

DETAILED DESCRIPTION OF THE PREFERRED EMBODIMENTS

Figure 1:
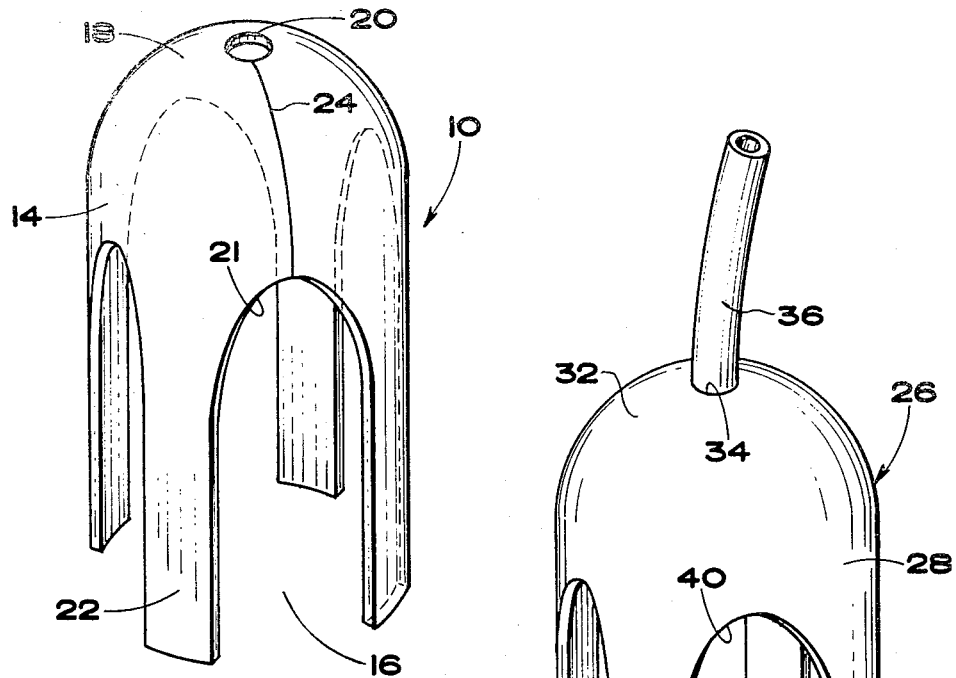
FIG. 1 is a perspective view of a catheter tube attachment embodying the invention.
Figure 2:
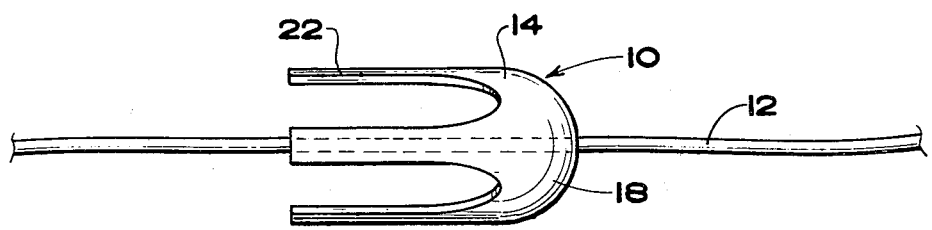
FIG. 2 is a side elevational view of the attachment shown in FIG. 1 installed on a catheter tube.

Referring to the drawings in detail, and particularly FIGS. 1 and 2, reference character 10 generally indicates an attachment for use in combination with a catheter tube 12. The attachment 10 comprises a substantially cylindrical housing 14 preferably constructed from a suitable plastic material which is non-abrasive when placed against the skin or flesh of a patient, and which is relatively rigid, but sufficiently yieldable for facilitating use thereof, as will be hereinafter set forth. The housing 14 is open at one end 16 thereof and the opposite end is closed by an arcuate or substantially spherical wall 18. A centrally disposd aperture 20 is provided in the closed end 18 and is of a diametric size for snugly receiving the tube 12 therethrough.

The housing 14 is provided with a plurality of circumferentially spaced openings 21 providing a hiatus between each adjacent pair of axially extending fingers 22 which terminate at the open end 16. Each hiatus is preferably substantially arch shaped, but not limited thereto, and whereas four fingers 22 are shown in the drawings, it will be apparent that substantially any desired number of the fingers may be provided, as desired. It may also be preferable to provide a slit 24 in the closed end 18 and extending from the aperture 20 to any of hiatus between an adjacent pair of the fingers 22 for facilitating disposition of the tube 12 in the aperture 20, as will be hereinafter set forth.

In use, the attachment 10 is disposed on the tube 12 in any suitable manner, such as by inserting one end (not shown) of the tube through the aperture 20 and manually sliding the housing 14 along the tube to position the housing as desired between the outer end of the tube and the usual catheter collector vessel (not shown). Alternately, it may be desirable to place the housing 14 over the tube 12 in a transverse direction by forcing the tube 12 through the slit 24 until the tube 12 reaches the aperture 20.

The outer end of the catheter tube may then be inserted through the urethra of the patient (not shown) in the usual manner, and the housing 14 may be moved longitudinally along the tube 12 for engagement with the outer end of the male member. The housing 14 may then be secured in position around the male member in any well known or suitable manner for retaining the housing in position as long as the catheter is in use, and as will be hereinafter set forth in detail. The aperture 20 is in a snug engagement with the outer periphery of the tube 12 and thus substantially precludes relative movement between the tube and the flesh of the male member. Thus, as the patient moves the discomfort of the use of the catheter tube is greatly allievated.

Figure 3:
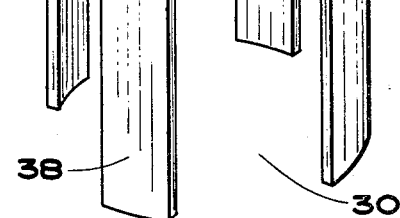
FIG. 3 is a perspective view of a modified form of attachment for a catheter tube.

Referring now to FIG. 3, a modified catheter tube attachment is generally indicated at 26 which comprises a housing 28 similar to the housing 18 and having one end 30 open and the opposite end closed by an arcuate or spherical wall 32. The wall 32 is provided with a centrally disposed bore or aperture 34 having a tubular member 36 secured therein in any suitable manner or integral with the housing 28, as desired. The tubular member 36 is preferably constructed from a yieldable or flexible material, and extends substantially axially outwardly from the wall 32 as clearly shown in the drawings. The housing 28 is provided with a plurality of circumferentially spaced axially extending fingers 38 similar to the fingers 22 at the open end 30 thereof, and a hiatus 40 is interposed between adjacent pair of the fingers 38. In this embodiment, the tube 12 may be inserted longitudinally through the tubular member 36 whereby the tube 12 extends through and beyond the housing 28. The housing 28 may be manually adjusted along the length of the tube 12 for achieving the proper spacing therefor as hereinbefore set forth. The use of the attachment 26 is substantially the same as the use of the attachment 10, and functions for greatly allieviating or reducing the discomfort of the use of a catheter tube by a male patient.

Figure 4:
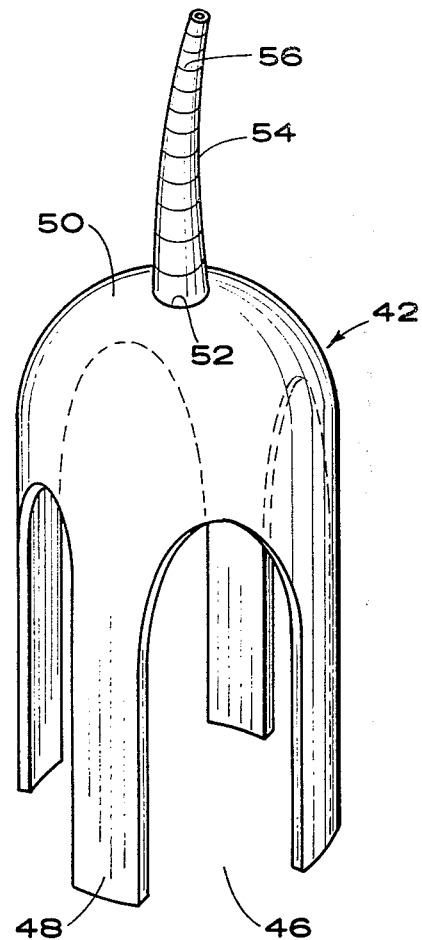
FIG. 4 is a perspective view of still another modified attachment for a catheter tube.

FIG. 4 illustrates a still further modified catheter tube attachment generally indicated at 42 which comprises a housing 44 similar to the housing 18 and 32. The housing 44 is open at one end 46 thereof, and a plurality of axially extending circumferentially spaced fingers 48 are provided at the open end 46 as hereinbefore set forth. The opposite end of the housing 44 is closed by an arcuate or spherical wall 50, and a centrally disposed aperture 52 is provided in the wall 50. A tubular member 54 is suitably secured to the aperture 52, or may be integral with the housing 44, as desired, and the tubular member 54 extends axially outwardly from the wall 50.

Since the catheter tubing 12 is frequently manufactured in a variety of diametric sizes, it is sometimes desirable to provide a means for adjusting the attachment 42 for use with substantially any diameter size tubing. Consequently, the element 54 is of a tapered or frusto-conical configuration whereby the outer sidewalls thereof converge in a direction toward the outer open end thereof, with the inner periphery of the element 54 being substantially circular in cross sectional configuration throughout the entire length thereof and having progressively increasing diametric sizes in a direction from the outer end toward the wall 50. A plurality of longitudinally spaced markings or indicia 56 is suitably inscribed around the outer periphery of the tubular member 54, with each marking 56 being positioned along the length of the element 54 in such a manner as to indicate the size of the internal diameter of the tubular member 54 immediately adjacent the respective marking. In this manner, the element 54 may be readily manually cut or severed along the particular marking indicating an internal diameter for the element 54 corresponding to the outer diameter of the tube 12 to be utilized therewith. Thus, the device 42 may be efficiently utilized with tubing 12 of substantially any diametric size.

Figure 7:
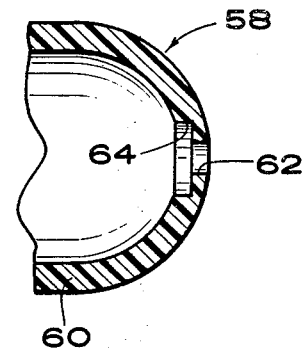
FIG. 7 is a sectional view of a portion of a still further modified catheter tube attachment embodying the invention.

Referring now to FIG. 7, a still further modified attachment for catheter tubes is generally indicated at 58 and comprises a housing 60 substantially identical to the housings 14, 26 and 42 with a substantially centrally disposed aperture 62 provided in the closed end thereof as hereinbefore set forth. In addition, it may be preferable to provide a relief port or recess portion 64 at the inner end of the aperture 62 to reduce chafing, or the like, of the flesh disposed adjacent the inner periphery of the housing 60, and particularly the portions of the flesh disposed at the proximity of the aperture 62. Of course, the housing 60 may also be provided with an axially outwardly extending tubular member such as the elements 36 and 54, if desired.

Figure 5:
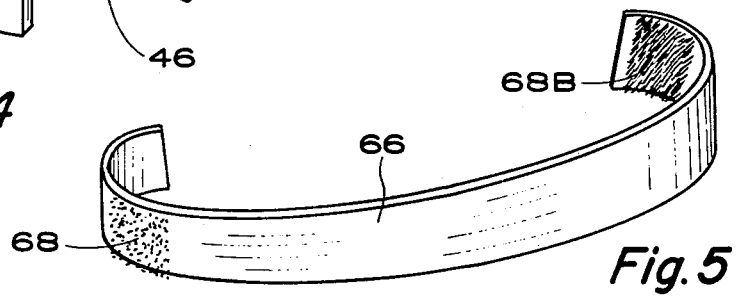
FIG. 5 is a perspective view of securing strap means for use with a catheter tube attachment embodying the invention.
Figure 6:
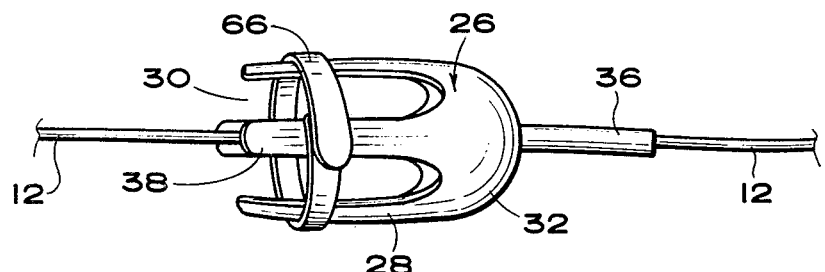
FIG. 6 is a perspective view of a catheter tube embodying the invention and illustrated in combination with the securing strap means.

The use of all of the embodiments shown herein is substantially identical and as hereinbefore set forth, the outer end of the tube 12 may be inserted through the urethra of the patient in the usual or well known manner and secured in position in the normal manner for directing urine into the catheter collection vessel (not shown). When the tube 12 has been thus been properly installed on the patient, the attachment 26 may be manually moved longitudinally along the outer periphery of the tube for receiving the outer end of the male member (not shown) therein. When the housing has been snugly and comfortably positioned on the male member, the fingers 38 may be manually moved radially inwardly for resting against the outer periphery of the member, and a suitable strap member 66 may be manually wrapped around the outer periphery of the fingers 38 for retaining the fingers in a snug engagement with the member. The strap 66 as shown herein is preferably provided with suitable fastening means, such as Velcro (a trademark of Velcro Corp.) as indicated at 68A and 68B in FIG. 5, whereby the tape or strap 66 may be quickly and easily secured in place around the fingers 38. It will be readily apparent that the attachment 26 may be readily removed from engagement with the male member by removing the strap 66 from engagement with the fingers 38 whereby the "memory" feature of the material from which the housing 28 is constructed will cause the fingers to move away from the snug engagement with the outer periphery of the member. The attachment 26 may then be moved longitudinally along the tube 12 in a direction away from the member, and the catheter tube may be removed from the patient in the usual or well known manner.

Figure 8:
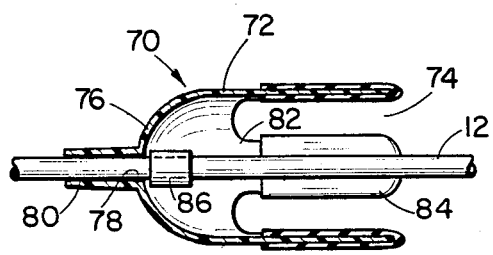
FIG. 8 is a sectional view of another modified catheter tube attachment embodying the invention.

FIG. 8 illustrates still another catheter tube attachment 70 comprising a housing 72 generally similar to the housings 18 and 28 and having one end 74 open and the opposite end closed by an arcuate wall 76. the wall 76 is provided with a central port or opening 78 having an outwardly extending tube member 80 for receiving the catheter tube 12 therethrough as hereinbefore set forth. The housing 72 is preferably constructed from a suitable flexible or yieldable material and is provided with axially extending circumferentially spaced fingers 82 at the open end 74 thereof for engagement with the male member as hereinbefore set forth. It is preferable to provide a covering 84 around the outer ends of the fingers 82, said covering being constructed from a soft or flexible material for increasing the comfort of the engagement of the fingers 82 with the male member. In addition, a relatively short tube or sleeve member 86 is secured around the outer periphery of the catheter tube 12 and disposed within the interior of the housing 72 in the proximity of the port 78 for substantially precluding any accidental withdrawal of the catheter tube 12 from the housing 72, such as in the event of the application of a sharp or sudden longitudinal force along the tube 12. In addition, the sleeve member 86 may provide a sizing function with regard to the engagement of the inner periphery of the housing 72 with the outer periphery of the male member. For example, if the male member is not in engagement with the arcuate end 76 for any reason, the sleeve 86 may compensate for any misalignment therebetween and facilitating holding of the catheter tube 12 against independent movement at the outer end of the male member.

From the foregoing it will be apparent that the present invention provides a novel attachment for catheter tubes which comprises a substantially cylindrical housing having one end open and one end closed by a spherical wall, with a plurality of circumferentially spaced axially extending fingers being provided at the open end. An aperture is provided at the closed end of the housing for receiving the catheter tube therethrough whereby interferences with the normal installation of the tube on a patient is precluded. The attchment may be quickly and easily placed over the male member of a patient subsequent to the installation of the catheter tube, and may be easily secured in position thereon. The attachment functions to substantially preclude any relative movement between the tube and the male member, thus allievating discomfort for the patient during use.

What is claimed is:

1. An independent attachment for a catheter tube and comprising relatively rigid housing means having one open end and one closed end, said closed end being provided with aperture means for receiving the catheter tube therethrough, said housing means being movable longitudinally along the outer periphery of the catheter tube for receiving a male member through the open end thereof, means for securing the housing means directly to the male member for extended time periods for isolating movement of the catheter tube from the male member for comfort of the male member, wherein the aperture means comprises an aperture provided in the closed end of the housing, and a frusto-conical tubing means extending axially outwardly from said aperture for receiving the tube therethrough, and wherein suitable indicia is provided on the outer periphery of the frusto-conical tubing means corresponding to the internal diameter of the tubing means in alignment therewith for facilitating use of the attachment with catheter tubes of substantially any diametric size.

2. An independent attachment for a catheter tube and comprising relatively rigid housing means having one open end and one closed end, said closed end being provided with aperture means for receiving the catheter tube therethrough, said housing means being movable longitudinally along the outer periphery of the catheter tube for receiving a male member through the open end thereof, means for securing the housing means directly to the male member for extended time periods for isolating movement of the catheter tube from the male member for comfort of the male member, and including sleeve means disposed within the housing means in the proximity of the aperture means for receiving the catheter tube therethrough for movement therewith for precluding accidental withdrawal of the catheter tube from the housing means.

3. An attachment as set forth in claim 2 wherein the closed end of the housing means is substantially spherical for comfortably receiving the outer end of the male member therein.

4. An attachment as set forth in claim 2 wherein the aperture means comprises an aperture provided in the closed end of the housing means, and tubular means extending axially outwardly therefrom for receiving the catheter tube therethrough.

5. An attachment as set forth in claim 2 wherein a plurality of circumferentially spaced fingers are provided around the open end of the housing means and extend axially outwardly for disposition around the outer pheriphery of the male member.

6. An attachment as set forth in claim 5 wherein the relatively rigid housing means is constructed of a material sufficiently yieldable for facilitating radially inward movement of the fingers into a snug engagement with the outer periphery of the male member for facilitating securing of the housing means thereon.

7. An attachment as set forth in claim 5 wherein the attachment means comprises a strap adapted for being wrapped around the outer periphery of the fingers for securing the attachment in position on the male member, and having securing means for removably securing the strap in position.

8. An attachment as set forth in claim 7 wherein the attachment means is Velcro.

9. An attachment as set forth in claim 2 and including a relief recess on the inner periphery of the closed end of the housing means conterminous with the aperture means for increasing the comfort of the patient.

10. An attachment as set forth in claim 2 wherein protective covering means is provided around the outer end of the open end of the housing for comfort of the patient.

* * * * *